(12) United States Patent
Takaishi

(10) Patent No.: US 9,078,790 B2
(45) Date of Patent: Jul. 14, 2015

(54) ABSORBENT ARTICLE

(75) Inventor: Mina Takaishi, Sakura (JP)

(73) Assignee: Daio Paper Corporation, Sakura-shi (JP)

( * ) Notice: Subject to any disclaimer, the term of this patent is extended or adjusted under 35 U.S.C. 154(b) by 181 days.

(21) Appl. No.: 13/581,084

(22) PCT Filed: Feb. 24, 2011

(86) PCT No.: PCT/JP2011/054109
§ 371 (c)(1),
(2), (4) Date: Aug. 24, 2012

(87) PCT Pub. No.: WO2011/105476
PCT Pub. Date: Sep. 1, 2011

(65) Prior Publication Data
US 2012/0323207 A1    Dec. 20, 2012

(30) Foreign Application Priority Data
Feb. 26, 2010  (JP) ................................ 2010-043230

(51) Int. Cl.
*A61F 13/15*      (2006.01)
*A61F 13/494*     (2006.01)
(Continued)

(52) U.S. Cl.
CPC ......... *A61F 13/49473* (2013.01); *A61F 13/495* (2013.01); *A61F 13/4946* (2013.01); *A61F 2013/4575* (2013.01);
(Continued)

(58) Field of Classification Search
CPC ............ A61F 13/49426; A61F 13/532; A61F 13/534; A61F 13/535; A61F 13/537; A61F 13/539; A61F 2013/4568; A61F 2013/4575; A61F 2013/4581; A61F 2013/530868; A61F 2013/5355; A61F 2013/53765
USPC ...................... 604/385.101, 385.19
See application file for complete search history.

(56) References Cited

U.S. PATENT DOCUMENTS 4,642,110 A * 2/1987 Dudek ..................... 604/385.21
4,735,624 A * 4/1988 Mazars ........................ 604/378
(Continued)

FOREIGN PATENT DOCUMENTS

CN    1262089A A1    8/2000
JP    09-506528 A    6/1997
(Continued)

*Primary Examiner* — Lynne Anderson
(74) *Attorney, Agent, or Firm* — Arthur M. Reginelli; Renner Kenner

(57) ABSTRACT

An absorbent article 200 has an improved ability to prevent the sacral part and coccygeal part being soiled by urine. The absorbent article 200 has a lower layer absorbent part 10 and, positioned above this, an upper layer absorbent part 20. Within the upper layer absorbent part 20, an upper layer front side portion 20F constituting the front side with respect to a coccyx facing portion TP is formed by a left side portion 30 and a right side portion 40. Their side edges facing the center in the width direction are configured to align with or come close to each other at a back rear end portion, extend forward from the back rear end portion with an increasing separation distance therebetween. The left side portion and the right side portion rise toward the skin of a wearer by contractile action of the tip-portion resilient and elastic member. Further, a clearance between an upper layer back rear side portion 20B and the lower layer absorbent part 10 is formed as a pocket 50 with an entrance at the separation section between the right side portion 40 and the left side portion 30.

7 Claims, 10 Drawing Sheets

(51) Int. Cl.
*A61F 13/495* (2006.01)
*A61F 13/45* (2006.01)
*A61F 13/535* (2006.01)
*A61F 13/534* (2006.01)

(52) U.S. Cl.
CPC   *A61F 2013/4581* (2013.01); *A61F 2013/5355* (2013.01); *A61F 2013/53445* (2013.01)

(56) References Cited

U.S. PATENT DOCUMENTS

| | | | | |
|---|---|---|---|---|
| 5,176,672 | A | * | 1/1993 | Bruemmer et al. ...... 604/385.19 |
| 5,624,422 | A | * | 4/1997 | Allen ...................... 604/385.23 |
| 5,779,690 | A | | 7/1998 | Gustafsson |
| 6,248,098 | B1 | * | 6/2001 | Sayama ................... 604/385.28 |
| 6,406,465 | B1 | | 6/2002 | Otsubo |
| 7,993,314 | B2 | * | 8/2011 | Asp et al. ...................... 604/348 |
| 8,048,052 | B2 | * | 11/2011 | Kurihara .................. 604/385.14 |
| 2006/0135931 | A1 | | 6/2006 | Suzuki et al. |

FOREIGN PATENT DOCUMENTS

| | | |
|---|---|---|
| JP | 2005-279004 A | 10/2005 |
| JP | 2006-174966 A | 7/2006 |
| JP | 2007-14705 A | 1/2007 |
| JP | 2009-112590 A | 5/2009 |
| JP | 2009-125203 | 6/2009 |
| JP | 2009-125338 A | 6/2009 |

* cited by examiner

ABSORBENT ARTICLE

TECHNICAL FIELD

The present invention relates to absorbent articles reducing urine soiling of a gluteal part.

BACKGROUND ART

Pressure ulcers are prone to develop on those who are confined to bed or wheelchair and those who cannot turn over or reposition themselves in bed, in particular, at body parts with bony prominences apt to be subjected to compression, for example, lower backs, buttocks, and the like. The direct cause of pressure ulcers is cessation of blood flow due to local compression. Further, if the skin is continuously exposed to liquid matters such as urine and stool for a long time, the surface of the skin is weakened and likely to be damaged, which is also prone to cause pressure ulcers.

Conventional absorbent articles allow urine to run in a clearance between the crotch portion of a wearer and the article and move over the skin of the wearer, and wet the sacrum and coccyx parts with a tendency to have pressure ulcers, whereby pressure ulcers become likely to develop there. Such a clearance is preferred in terms of efficient use of the absorbent body by spreading urine over the entire absorbent body extending almost entirely from the ventral to back sides, but this is not preferred in terms of prevention of pressure ulcers.

To solve the foregoing problem, there have been suggested absorbent articles with pockets for holding body waste (refer to Patent Literatures 1 and 2). However, each of these articles produces a clearance between the entry edge of the pocket and the body of a wearer, and hence is not capable of guiding urine running over the skin into the pocket.

CITATION LIST

Patent Literatures

Patent Literature 1: JP 2005-279004 A
Patent Literature 2: JP 2009-125203 A

SUMMARY OF INVENTION

Technical Problem

Therefore, a main object of the present invention is to provide an absorbent article improved in capability of preventing urine soiling of sacrum and coccyx parts.

Solution to Problem

The present invention solving the foregoing problem is as follows:
<Invention According to Claim 1>
An absorbent article, including a coccyx facing portion; an article front side portion constituting a front side of the coccyx facing portion; and an article rear side portion including the coccyx facing portion on a rear side with respect to the article front side portion, wherein a lower layer absorbent part and an upper layer absorbent part positioned above the lower layer absorbent part, each extend in a front-rear direction from the article front side portion to the article rear side portion, the lower layer absorbent part being configured to absorb body waste from at least a surface facing the upper layer absorbent part, and the upper layer absorbent part being configured to absorb body waste from at least a surface facing the lower layer absorbent part, the upper layer absorbent part is formed by an upper layer front side portion constituting a front side of the coccyx facing portion and an upper layer rear side portion including the coccyx facing portion on a rear side with respect to the upper layer front side portion, the upper layer front side portion is formed by a left side portion positioned on a left side with respect to a center in a wide direction and a right side portion positioned on a right side of the same; a side edge of the left side portion facing the center in the width direction and a side edge of the right side portion facing the center in the width direction, align with or come close to each other at a rear end portion, extend forward from the rear end portion with an increasing separation distance therebetween, and reach a groin part along a base of a leg of a wearer; and the lower layer absorbent part is exposed at a separation section between the side edge of the left side portion facing the center in the width direction and the side edge of the right side portion facing the center in the width direction, the right and left side portions are fixed at side edges facing an outside in the width direction to a surface of the lower layer absorbent part; the right and left side portions are fixed to the surface of the lower layer absorbent part at front ends of portions closer to the center in the width direction than the fixed sections but are not fixed to the surface of the lower layer absorbent part at free sections other than the front end portions; and a tip-portion resilient and elastic member is fixed to edges of the free sections facing the center in the width direction, in a state of being stretched along the edges, and a clearance between the upper layer rear side portion and the lower layer absorbent part is formed as a pocket with an entrance at the separation section between the right and left side portions of the upper layer front side portion.

(Operation and Effect)

In the present invention, of the upper layer absorbent part, the upper layer front side portion positioned on the front side with respect to the coccyx facing portion is divided into the right and left side portions, the side edges of these portions facing the center in the width direction align with or come close to each other at the rear end portion and extend forward from the rear end portion with an increasing separation distance therebetween, and these right and left side portions rise toward the skin of a wearer by contractile action of the tip-portion resilient and elastic member. In addition, the pocket with an entrance at the separation section between the right and left side portions is formed between the upper layer rear side portion and the lower layer absorbent part. Accordingly, an entrance edge of the pocket is formed by the side edges of the right and left side portions at the upper layer front side portion facing the center in the width direction. The pocket has, at a rear end portion, side edges aligning with or coming close to each other to form a chevron shape and fit to the anus or its neighboring region of the wearer, and the pocket has, on a front side of the rear end portion, the side edges fitting to the groin part of the wearer along the bases of legs. As a result, it is possible to fit the upper layer absorbent part to the crotch portion of the wearer, guide urine running over the skin to the pocket, and absorb urine by at least one of the upper layer absorbent part and the lower layer absorbent part, thereby reducing urine soiling of the coccyx and sacrum parts.

<Invention According to Claim 2>
The absorbent article according to Claim 1, wherein a plurality of the tip-portion resilient and elastic members is provided at the right and left side portions, with intervals therebetween in the width direction, such that tip-portion resilient and elastic members nearer the center in the width direction have a higher extension ratio.

(Operation and Effect)

When a plurality of the tip-portion resilient and elastic members for raising the right and left side portions of the upper layer front side portion is provided such that the tip-portion resilient and elastic members nearer the center in the width direction have a higher extension ratio, the right and left side portions of the upper layer front side portion warps and rises so as to be more inclined with increasing proximity to the center from the outside in the width direction (in other words, such that the side surfaces of the lower layer absorbent part bulge). This improves significantly the absorbent article in fitting property to the anus or its neighboring region and also allows the absorbent article to fit preferably to the bases of the legs in a linear form.

<Invention According to Claim 3>

The absorbent article according to Claim 1 or 2, wherein the upper layer absorbent part is made thinner at, at least one of the sacrum facing portion and the coccyx facing portion of the upper layer rear side portion than a surrounding part thereof.

(Operation and Effect)

When the upper layer absorbent part is laid over the lower layer absorbent part, the absorbent article increases in thickness, which may result in concentration of pressure on the sacrum and the coccyx protruding from the body surface of the wearer. Such pressure causes pressure ulcers as described above. Meanwhile, when the upper layer absorbent part is made thinner at the sacrum facing portion and/or the coccyx facing portion than the surrounding part as described above, it is preferably possible to lessen concentration of pressure on the sacrum and the coccyx.

<Invention According to Claim 4>

The absorbent article according to any one of Claims 1 to 3, wherein the upper layer absorbent part has an upper layer absorbent body, and a liquid impervious sheet covering a side of the upper layer absorbent body opposite to a side facing the lower layer absorbent part.

(Operation and Effect)

When the liquid impervious sheet covers the surface of the upper layer absorbent body at the side opposite to that facing the lower layer absorbent part, it is preferably possible to prevent that body waste guided into the pocket flows back to the skin of the wearer via the upper layer absorbent part.

Advantageous Effects of Invention

As in the foregoing, according to the present invention, it is possible to produce an advantage of improving the absorbent article in capability of preventing urine soiling of the sacrum and coccyx parts of the wearer, and the like.

DESCRIPTION OF EMBODIMENTS

Figure 1:
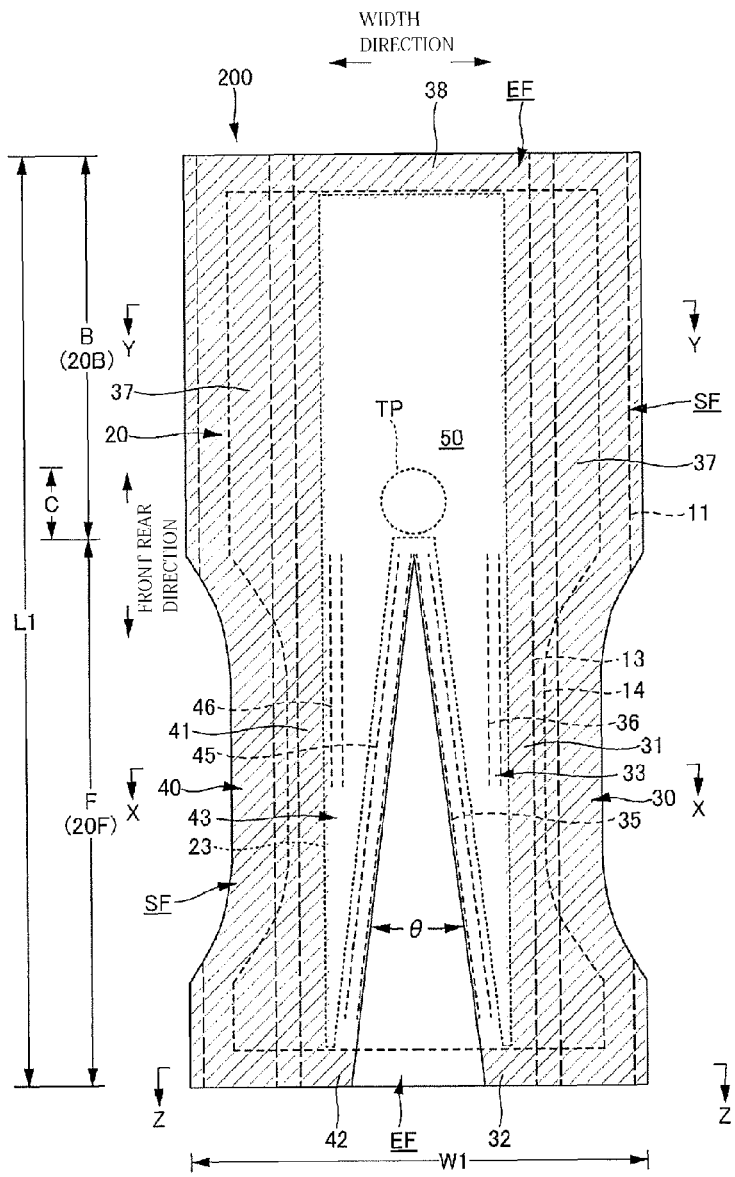
FIG. 1 is a plane view showing an inner side of an absorbent pad in a developed state.
Figure 2:
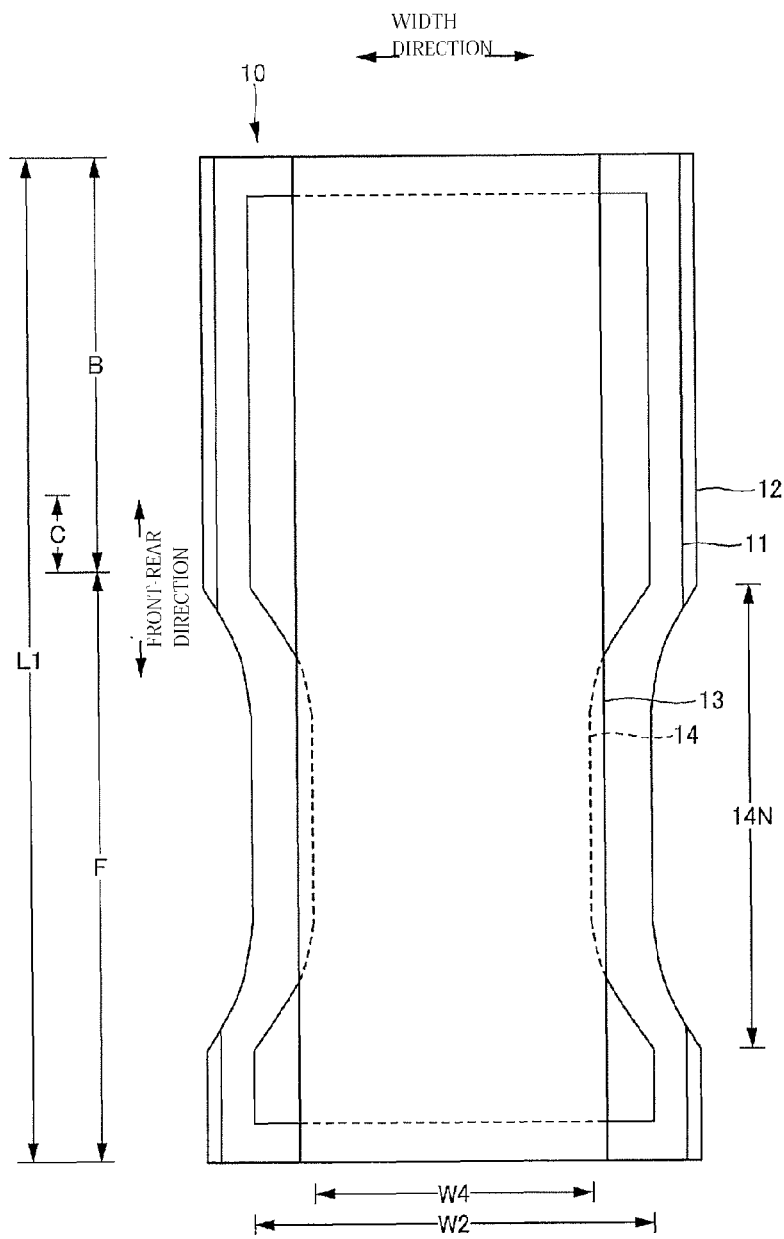
FIG. 2 is a plane view showing only a lower layer absorbent part.
Figure 3:
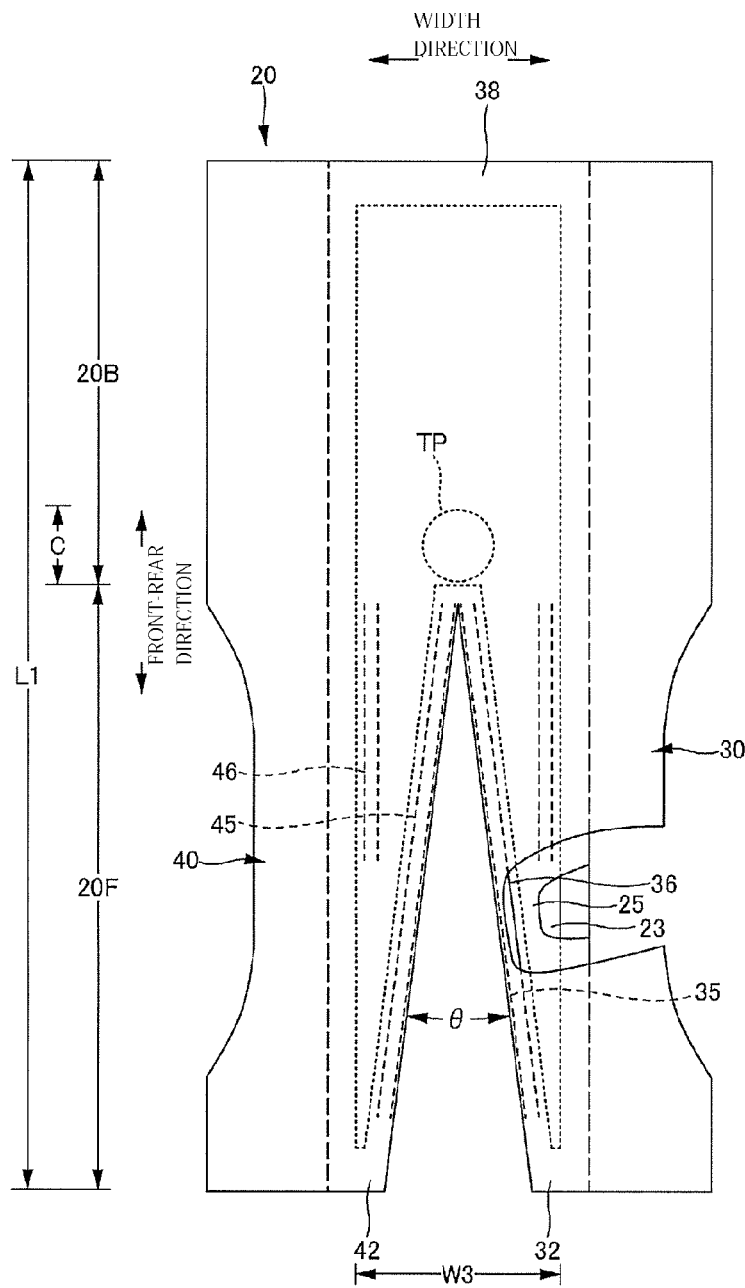
FIG. 3 is a partially fractured plane view showing only an upper layer absorbent part.
Figure 4:
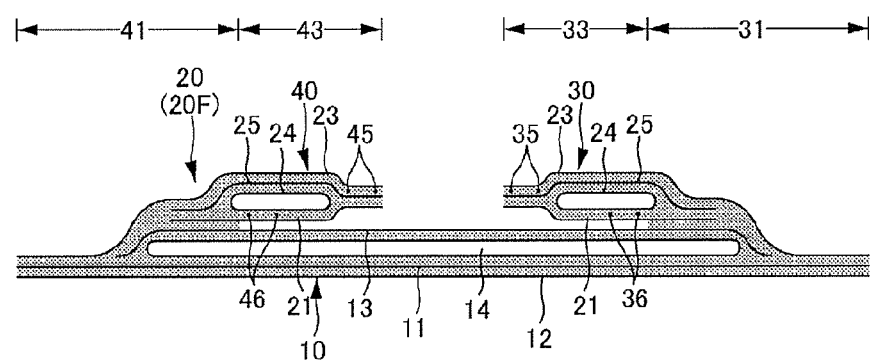
FIG. 4 is a cross section view of FIG. 1 taken along a line X-X.
Figure 5:
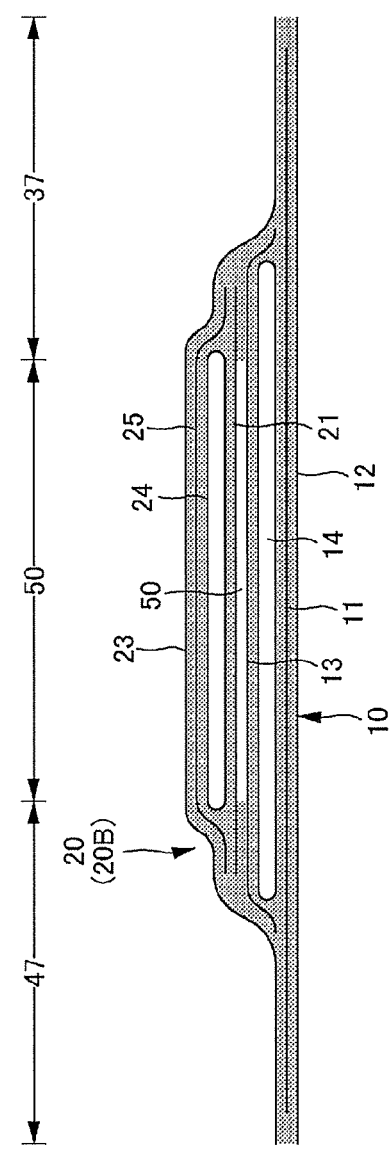
FIG. 5 is a cross section view of FIG. 1 taken along a line Y-Y.
Figure 6:
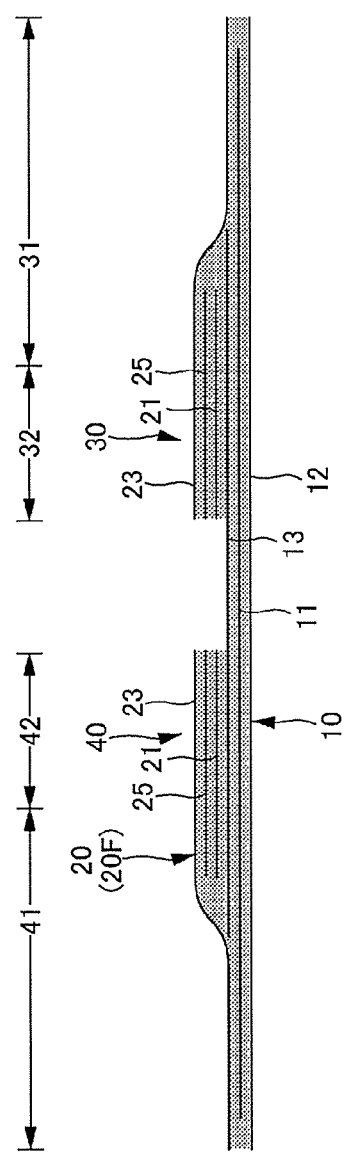
FIG. 6 is a cross section view of FIG. 1 taken along a line Z-Z.

One embodiment of the present invention will be described below in detail with reference to the accompanied drawings. The terms "coccyx facing portion," "sacrum facing portion," and "crotch portion" refer to parts facing the coccyx, sacrum, and crotch of a wearer in use, and vary depending on a product. Dotted patterns in the cross section views denote fixed sections formed by adhesion with a hot-met adhesive or fusion bonding of materials.

FIGS. 1 to 8 show an example of an absorbent pad 200 according to the present invention. The absorbent pad 200 has a coccyx facing portion C, an article front side portion F constituting a front side of the coccyx facing portion C, and an article rear side portion B including the coccyx facing portion C on a rear side with respect to the article front side portion F. Dimensions of these components can be decided as appropriate, and for example, an article entire length (front-rear length) L1 may be about 350 to 700 mm, an article entire width W1 may be about 130 to 400 mm. In this case, a front-rear length of the front side portion F may be about 150 to 400 mm, and a front-rear length of the rear side portion B may be about 200 to 300 mm, and a front-rear length of the coccyx facing portion C may be about 40 to 100 mm.

The absorbent pad 200 has a lower layer absorbent part 10 and an upper layer absorbent part 20 positioned above the lower layer absorbent part 10, each of which extends in the front-rear direction from the article front side portion F to the article rear side portion B. In the illustrated example, the lower layer absorbent part 10 and the upper layer absorbent part 20 are both provided along the entire length of the article. Alternatively, either one of the parts may be made shorter than the other, for example, the upper layer absorbent part 20 may be made shorter than the lower layer absorbent part 10.

(Lower Layer Absorbent Part)

The lower layer absorbent part 10 has a basic structure in which a lower layer absorbent body 14 intervenes between an inner surface of a lower layer back side sheet 11 and a lower layer face side sheet 13.

More specifically, the lower layer absorbent body 14 may basically use an accumulated body of pulp fibers, an assembly of filaments of cellulose acetate or the like, or a non-woven fabric, and as necessary, may use high-absorbent polymer particles or the like mixed into or adhered to the basic material. If the high-absorbent polymer particles are mixed or the like, the lower layer absorbent body 14 may be covered as necessary with a liquid pervious package sheet of crepe paper or the like (not shown).

Basis weights of fibers and high-absorbent polymers in the lower layer absorbent body 14 can be decided as appropriate. Preferably, the basis weight of fibers is about 100 to 600 g/m$^2$, and the basis weight of absorbent polymers is about 0 to 400 g/m$^2$.

In addition, the lower layer absorbent body 14 may be shaped such that the crotch portion constitutes a narrower portion 14N narrower than both sides thereof in the front-rear direction as in the illustrated example, or may have any other appropriate shape such as a belt-like shape in which a front side portion is relatively wider than a rear side portion, a rectangular shape, a trapezoidal shape, or the like. Dimensions of the lower layer absorbent body 14 can be decided as appropriate, and a front-rear length L2 of the lower layer absorbent body 14 may be about 85 to 95% of the article entire length L1, and a width W2 of the lower layer absorbent body 14 may be about 70 to 95% of the article width W1. A minimum width W4 of the narrower portion 14N is preferably about 35 to 65% of the lower layer absorbent body width W2. If the article front end is defined as 0% and the article rear end 100%, a front end of the narrower portion 14N preferably falls within a range of 10 to 25%, and a rear end of the narrower portion 14N preferably falls within a range of 40 to 65%, a region with a minimum width W4 of the narrower portion 14N (minimum-width region) preferably falls within a range of 25 to 50%.

On the back side of the lower layer absorbent body 14, the lower layer back side sheet 11 is provided so as to run off a peripheral edge of the lower layer absorbent body 14. The lower layer back side sheet 11 may be a liquid impervious sheet or a liquid pervious sheet according to the product. The liquid impervious sheet may use a resin film such as a polyethylene film or the like, or a sheet with both a water shielding property and moisture permeability, in terms of prevention of stuffiness. Such a liquid impervious/moisture pervious sheet may use a microporous sheet obtained by melting and kneading an inorganic filling agent into an olefin resin such as polyethylene or polypropylene to thereby form a sheet and then extending the sheet in a uniaxial or biaxial direction, for example, or a water-repellent non-woven fabric obtained by subjecting a non-woven fabric to a water-repellent process using silicone or the like, for example.

An outer surface of the lower layer back side sheet 11 can be partially or entirely covered with an outer sheet 12 made of a non-woven fabric. The outer sheet 12 may use any publicly known non-woven fabric such as a spun-bonded non-woven fabric. Fiber materials usable for the non-woven fabric include synthetic fibers based on olefin such as polyethylene or polypropylene, polyester, amide, or the like, recycled fibers of rayon or cupra, or natural fibers of cotton or the like.

The face side of the lower layer absorbent body 14 is covered with the lower layer face side sheet 13. In the illustrated mode, the lower layer absorbent body 14 partially runs off the side edges of the lower layer face side sheet 13. Alternatively, the lower layer face side sheet 13 may be widened so that the side edges of the lower layer absorbent body 14 do not run off the lower layer face side sheet 13. The lower layer face side sheet 13 may use a porous or non-porous non-woven fabric or a liquid pervious sheet such as a perforated plastic sheet. The non-woven fabric may be any publicly known non-woven fabric such as an air-through non-woven fabric or a spun-lace non-woven fabric. Fiber materials usable for the non-woven fabric include synthetic fibers based on olefin such as polyethylene or polypropylene, polyester, amide, or the like, recycled fibers of rayon or cupra, or natural fibers of cotton or the like.

An intermediate sheet not shown may be intervened between the lower layer face side sheet 13 and the lower layer absorbent body 14. The intermediate sheet is provided to prevent back-flow of urine absorbed by the lower layer absorbent body 14. The intermediate sheet desirably uses a material with low water retentivity and high liquid permeability, for example, a high-bulk non-woven fabric, a mesh film, or the like. If the front end of the lower layer face side sheet 13 is defined as 0% and the rear end of the lower layer face side sheet 13 as 100%, a front end of the intermediate sheet preferably falls within a range of 0 to 11%, and a rear end of the intermediate sheet preferably falls within a range of 92 to 100%. In addition, a width of the intermediate sheet is preferably about 30 to 65% of the article width W1.

(Upper Layer Absorbent Part)

The upper layer absorbent part 20 has a basic structure in which an upper layer absorbent body 24 intervenes between an upper layer back side sheet 21 and an upper layer face side sheet 23.

The upper layer back side sheet 21 and the upper layer face side sheet 23 may use a material selected as appropriate from materials suitable for the lower layer face side sheet 13, and may use the same material as that of the lower layer face side sheet 13 or use a different material.

The upper layer absorbent body 24 may use a material selected as appropriate from materials suitable for the lower layer absorbent body 14, and may use the same material as that of the lower layer absorbent body 14 or use a different material. A width W3 of the upper layer absorbent body 24 is preferably narrower than the width W2 of the lower layer absorbent body 14, in particular, is preferably about 30 to 50% of the width W2 of the lower layer absorbent body 14. However, the width W3 may be the same as or wider than the width W2.

Further, as in the illustrated mode, it is preferred to make a liquid impervious sheet 25 intervene between the upper layer absorbent body 24 and the upper layer face side sheet 23. Instead of this or in addition to this, the upper layer face side sheet may be formed by a liquid impervious sheet. In either case, the liquid impervious sheet 25 may use a material selected as appropriate from materials suitable for the lower layer back side sheet 12, and may use the same material as that of the lower layer back side sheet 12 or may use a different material.

The front and rear end portions of the upper layer absorbent part 20 are formed by extending the upper layer back side sheet 21 and the upper layer face side sheet 23 on the front and rear sides with respect to the front and rear ends of the upper layer absorbent body 24 and attaching the extended sheets together. Meanwhile, the front and rear end portions of the lower layer absorbent part 10 are formed by extending the lower layer back side sheet 11, the outer sheet 12, and the lower layer face side sheet 13 on the front and rear sides with respect to the front and rear ends of the lower layer absorbent body 14 and attaching the extended sheets together. Accordingly, the front and rear end portions of the absorbent article 200 constitute end flap sections EF formed by attaching together the front and rear end portions of the lower layer absorbent part 10 and the front and rear end portions of the upper layer absorbent part 20, without intervention of the upper layer absorbent body 24 and the lower layer absorbent body 14.

In addition, side portions of the upper layer absorbent part 20 are formed by extending the upper layer back side sheet 21 and the upper layer face side sheet 23 laterally from the side edges of the upper layer absorbent body 24 and attaching the extended sheets together. Meanwhile, side portions of the lower layer absorbent part 10 are formed by extending the lower layer back side sheet 11, the outer sheet 12, and the lower layer face side sheet 13 laterally from the side edges of the lower layer absorbent body 14 and attaching the extended sheets together. Accordingly, the side portions of the absorbent article 200 constitute side flap sections SF formed by attaching together the side portions of the lower layer absorbent part 10 and the side portions of the upper layer absorbent part 20, without intervention of the upper layer absorbent body 24 and the lower layer absorbent body 14.

Characteristically, the upper layer absorbent part 20 is formed by an upper layer front side portion 20F constituting the front side of the coccyx facing portion TP and an upper layer rear side portion 20B including the coccyx facing portion TP on the rear side with respect to the upper layer front side portion 20F. In the illustrated example, a front end portion of the upper layer front side portion 20F reaches the front end portion of the article, and the rear end portion of the same reaches the rear end portion of the article.

In the foregoing arrangement, the upper layer front side portion 20F is formed by a left side portion 30 positioned on the left side with respect to the center in the width direction and a right side portion 40 positioned on the right side of the same. A side edge of the left side portion 30 facing the center in the width direction and a side edge of the right side portion 40 facing the center in the width direction align with or come close to each other at a rear end portion, extend forward from the rear end portion with an increasing separation distance therebetween, and reach the groin part of the wearer along the bases of legs. The lower layer absorbent part 10 is exposed at a separation section between the side edge of the left side portion 30 facing the center in the width direction and the side edge of the right side portion 40 facing the center in the width direction. Although the side edges of the left side portion 30 and the right side portion 40 facing the center in the width direction are arranged in a straight line (the side edges form a V shape) in the illustrated example, the side edges may be arranged in a curved line. An angle of intersection of these side edges (inner angle) θ can be decided as appropriate but is preferably about 20 to 50 degrees.

In addition, the left side portion 30 and the right side portion 40 of the upper layer front side portion 20 are fixed at side edges 31 and 41 facing the outside in the width direction to the surface of the lower layer absorbent part 10. At portions of the left side portion 30 and the right side portion 40 closer to the center in the width direction than the fixed sections 31 and 41, front ends 32 and 42 are fixed to the surface of the lower layer absorbent part 10, but portions 33 and 43 other than the front end portions are free sections not fixed to the surface of the lower layer absorbent part 10. Side edges of the fixed sections 31 and 41 facing the center in the width direction are preferably positioned closer to the center in the width direction than the side edges of the upper layer absorbent body 24 facing the outside in the width direction as in the illustrated example. However, the side edges of the fixed sections 31 and 41 may be positioned at the same position as that of the side edges of the upper layer absorbent boy 24 facing the outside in the width direction or may be positioned closer to the outside in the width direction than the same. The fixed sections 31 and 41 can be formed by adhesion with a hot-melt adhesive or by fusion bonding of materials.

At the left side portion 30 and the right side portion 40 of the upper layer front side portion 20F, tip-portion resilient and elastic members 35 and 45 are fixed with a hot-melt adhesive to the edges of the free sections 33 and 43 facing the center in the width direction, in a state of being stretched along the edges. The tip-portion resilient and elastic members 35 and 45 may use styrene rubber, olefin rubber, urethane rubber, ester rubber or the like, formed in the shape of threads, strings, belts, or the like (the same thing applies to base-portion resilient and elastic members described later). In the illustrated example, the tip-portion resilient and elastic members 35 and 45 are provided at the edges of the left side portion 30 and the right side portion 40 facing the center in the width direction without intervention of the upper layer absorbent body 24. Alternatively, the tip-portion resilient and elastic members 35 and 45 may be provided on the face or back side of the end portion of the upper layer absorbent body 24 facing the center in the width direction.

Further, as in the illustrated example, base-portion resilient and elastic members 36 and 46 may be fixed with a hot-melt adhesive or the like to the edges of the free sections 33 and 43 facing the outside in the width direction, in a state of being stretched along the edges. In this case, the base-portion resilient and elastic members 36 and 46 may be provided on the back side of the end portion of the upper layer absorbent body 24 facing the outside in the width direction, or may be provided on the face side of the same, or may be provided at portions of the free sections 33 and 43 facing the outside in the width direction without intervention of the upper layer absorbent body 24, if such portions exist.

Meanwhile, the upper layer rear side portion 20B has side portions 37 and a rear end portion 38 fixed to the surface of the lower layer absorbent part 10, a section surrounded by the fixed sections 37 and 38 is unfixed, and a portion between the unfixed section and the lower layer absorbent part 10 is configured as a pocket 50 with an entrance at a separation section between the left side portion 30 and the right side portion 40 of the upper layer front side portion 20F. The fixed sections of the upper layer rear side portion 20B can also be formed by adhesion with a hot-melt adhesive or by fusion bonding of materials. In particular, the fixed side sections 37 are desirably made continuous with the fixed right and left side sections 31 and 41 of the upper layer front side portion 20F.

Figure 7:
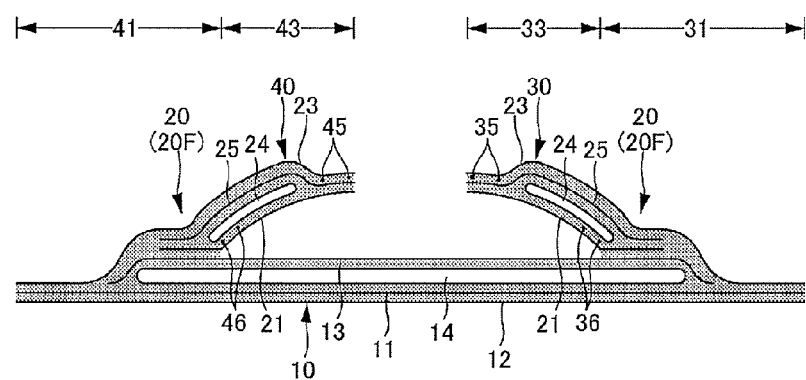
FIG. 7 is a cross section view of a crotch portion with rising of an upper layer front side portion.
Figure 8:
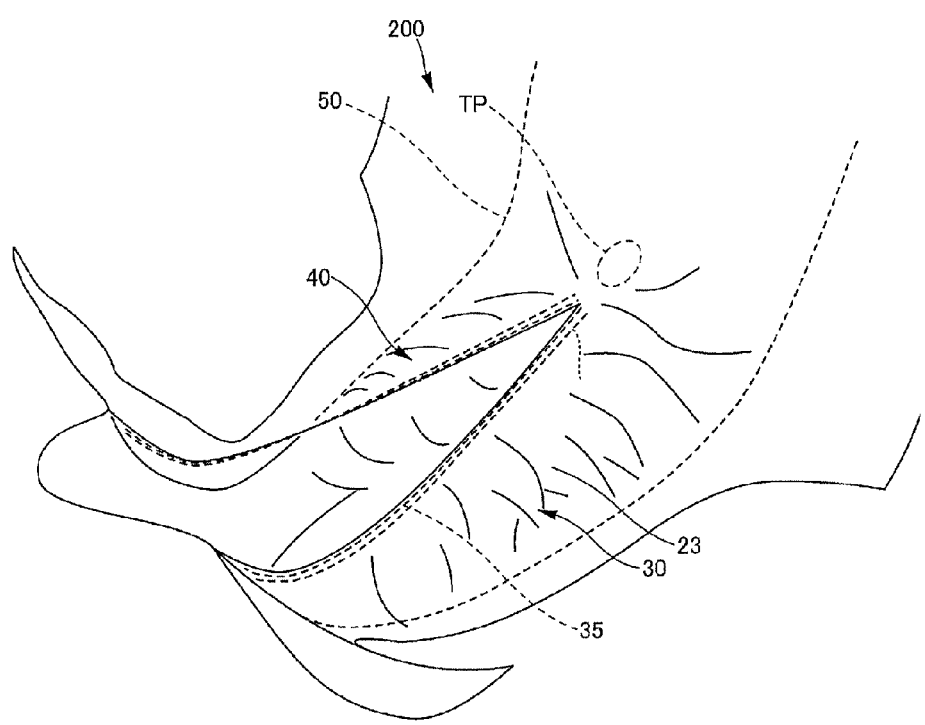
FIG. 8 is a perpendicular view of an absorbent article.

In the thus configured absorbent article, as shown in FIGS. 7 and 8, the left side portion 30 and the right side portion 40 of the upper layer front side portion 20F rise toward the skin of the wearer by contractile action of the tip-portion resilient and elastic members 35 and 45, and the separation section between the left side portion 30 and the right side portion 40 constitutes the entrance of the pocket 50 between the upper layer rear side portion 20B and the lower layer absorbent part 10. In addition, at the entrance edge portion of the pocket 50, side edges align with or come close to each other to form a chevron shape at the rear end portion of the upper layer front side portion 20F and fit to the anus or its neighboring region, and the side edges fit to the groin part of the wearer along the bases of the legs on the front side of the rear end portion of the upper layer front side portion 20F. As a result, it is possible to fit the upper layer absorbent part 20 to the crotch part of the wearer, guide urine running over the skin into the pocket 50, and absorb the urine by at least one of the upper layer absorbent part 20 and the lower layer absorbent part 10, thereby reducing urine soiling of the coccyx and sacrum parts of the wearer.

Figure 10:
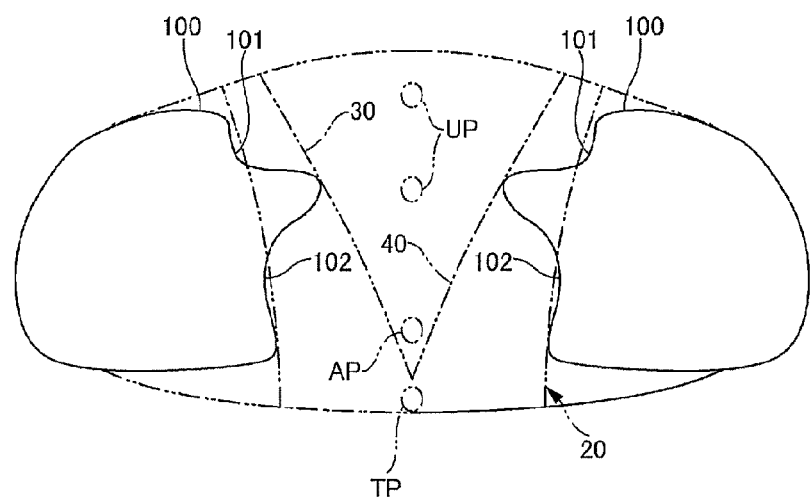
FIG. 10 is a schematic diagram for describing a fitting property of the upper layer front side portion with respect to the crotch portion.

Particularly in the case of the illustrated mode, when the left side portion 30 and the right side portion 40 of the upper layer front side portion 20F are arched so as to be less inclined with increasing proximity to the center from the outside in the width direction (in other words, such that the wearer-side surfaces bulge), the left side portion 30 and the right side portion 40 of the upper layer front side portion 20F rise in a chevron shape as shown in FIGS. 7 and 8, which preferably improves the absorbent article in fitting property with respect to recesses 101 on the inside of thighs and recesses 102 on the outside of the thighs of legs 100 as schematically shown in FIG. 10. To form this shape completely, it is preferred to provide the base-portion resilient and elastic members 36 and 46 on the back side of the upper layer absorbent body 24 at the edges of the free sections 33 and 43 facing the outside in the width direction. In the drawing, reference code UP denotes the positions of urination outlets, and reference code AP denotes the position of an anus.

In addition, as in the illustrated example, when the liquid impervious sheet 25 is provided to cover a surface of the upper layer absorbent body 24 at a side opposite to that facing the lower layer absorbent part 10, it is possible to prevent body waste guided into the pocket 50 from flowing back to the skin of the wearer via the upper layer absorbent part 20, which provides a greater advantage of reducing urine soiling of the coccyx and sacrum parts.

<Others>

Figure 9:
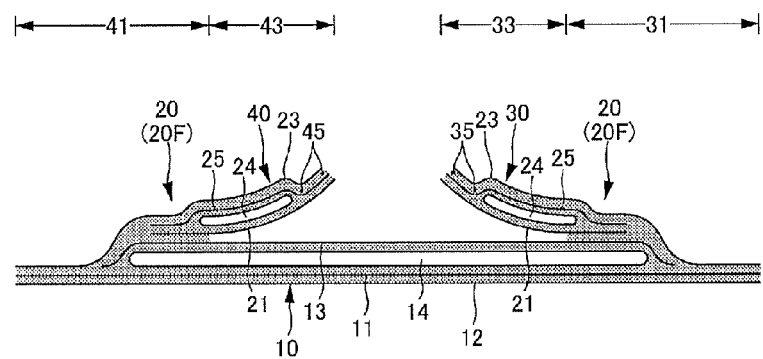
FIG. 9 is a cross section view of the crotch portion with rising of the upper layer front side portion.

(a) In another preferred mode as shown in FIG. 9, a plurality of the tip-portion resilient and elastic members 35 and 45 is provided at the left side portion 30 and the right side portion 40 of the upper layer front side portion 20F with intervals therebetween in the width direction such that the tip-portion resilient and elastic members 35 and 45 closer to the center in the width direction have a higher extension ratio. Accordingly, the left side portion 30 and the right side portion 40 of the upper layer front side portion 20F warp upward so as to be more inclined with increasing proximity to the center from the outside in the width direction (in other words, such that the lower layer absorbent part 10-side surfaces bulge), which significantly improves the absorbent article in fitting property with respect to the anus or its neighboring region and also allows the absorbent article to fit preferably to the bases of the legs in a linear form.

(b) If the upper layer absorbent part 20 is laid over the lower layer absorbent part 10, the absorbent body increases in thickness to concentrate pressure on the coccyx and the sacrum protruding from the surface of the body, which is not preferable from the viewpoint of prevention of pressure ulcers. Accordingly, it is preferred to make the upper layer absorbent part 20 thinner at the coccyx facing portion TP than a surrounding part to lessen concentration of pressure on the coccyx. Specifically, the coccyx facing portion TP of the upper layer absorbent part 20 can be made thinner than the surrounding part by providing the coccyx facing portion TP with concaves by embossing, or decreasing locally the basis weight of material at the coccyx facing portion TP, or forming the coccyx facing portion TP with through-holes by punching or molding, on the upper layer absorbent body 24. Instead of this or in addition to this, the upper layer absorbent part 20 can also be made thinner at the sacrum facing portion than a surrounding part. In addition, not only the upper layer absorbent part 20 but also the lower layer absorbent part 10 can be made thinner at the same portion(s).

Industrial Applicability

The present invention is applicable to absorbent pads, underpants-type or tape-type disposable diapers, and comprehensive absorbent articles.

BRIEF DESCRIPTION OF NUMERALS

10 . . . Upper layer absorbent part, 11 . . . Lower layer back side sheet, 12 . . . Outer sheet, 13 . . . Lower layer face side sheet, 14 . . . Lower layer absorbent body, 20 . . . Upper layer absorbent part, 21 . . . Upper layer back side sheet, 23 . . . Upper layer face side sheet, 24 . . . Upper layer absorbent body, 30 . . . Left side portion, 40 . . . Right side portion, 50 . . . Pocket The incention claimed is:

1. An absorbent article, comprising an article front side portion and an article rear side portion extending on a front side and a rear side with respect to a coccyx facing portion, respectively, wherein
a lower layer absorbent part and an upper layer absorbent part positioned above the lower layer absorbent part, each extend in a front-rear direction from the article front side portion to the article rear side portion, the lower layer absorbent part being configured to absorb body waste from at least a surface facing the upper layer absorbent part, and the upper layer absorbent part being configured to absorb body waste from at least a surface facing the lower layer absorbent part,
the upper layer absorbent part is formed by an upper layer front side portion constituting a front side of the coccyx facing portion and an upper layer rear side portion including the coccyx facing portion on a rear side with respect to the upper layer front side portion,
the upper layer front side portion is formed by a left side portion positioned on a left side with respect to a center in a wide direction and a right side portion positioned on a right side of the same; a side edge of the left side portion facing the center in the width direction and a side edge of the right side portion facing the center in the width direction, align with or come close to each other at a rear end portion, extend forward from the rear end portion with an increasing separation distance therebetween; and adapted to reach a groin part along a base of a leg of a wearer; and the lower layer absorbent part is exposed at a separation section between the side edge of the left side portion facing the center in the width direction, and the side edge of the right side portion facing the center in the width direction,
the right and left side portions are fixed at side edges facing an outside in the width direction to a surface of the lower layer absorbent part; the right and left side portions are fixed to the surface of the lower layer absorbent part at front ends of portions closer to the center in the width direction than the fixed sections but are not fixed to the surface of the lower layer absorbent part at free sections other than the front end portions; and a resilient and elastic member is fixed to edges of the free sections facing the center in the width direction proximate to the interval between the right and left side portion, in a state of being stretched along the edges,
these right and left side portions rise by contractile action of the tip-portion resilient and elastic member, and
a clearance between the upper layer rear side portion and the lower layer absorbent part is formed as a pocket with an entrance at the separation section between the right and left side portions of the upper layer front side portion.

2. The absorbent article according to claim 1, wherein a plurality of the tip-potion resilient and elastic members is provided at the right and left side portions, with intervals therebetween in the width direction, such that resilient and elastic members nearer the center in the width direction have a higher extension ratio.

3. The absorbent article according to claim 2, wherein the upper layer absorbent part is made thinner at, at least one of the sacrum facing portion and the coccyx facing portion of the upper layer rear side portion than a surrounding part thereof.

4. The absorbent article according to claim 1, wherein the upper layer absorbent part has an upper layer absorbent body, and a liquid impervious sheet covering a side of the upper layer absorbent body opposite to a side facing the lower layer absorbent part.

5. The absorbent article according to claim 1, wherein the upper layer absorbent part is made thinner at, at least one of the sacrum facing portionand the coccyx facing portion of the upper layer rear side portion than a surrounding part thereof.

6. The absorbent article according to claim 5, wherein the upper layer absorbent part has an upper layer absorbent body, and a liquid impervious sheet covering a side of the upper layer absorbent body opposite to a side facing the lower layer absorbent part.

7. The absorbent article according to claim 1, wherein the upper layer absorbent part has an upper layer absorbent body, and a liquid impervious sheet covering a side of the upper layer absorbent body opposite to a side facing the lower layer absorbent part.

\* \* \* \* \*